United States Patent [19]

Koyama et al.

[11] 3,963,712

[45] June 15, 1976

[54] 3-HALO-CEPHALOSPORINS

[75] Inventors: Masao Koyama; Shigeo Seki, both of Tokyo, Japan

[73] Assignee: Meiji Seika Kaisha, Ltd., Tokyo, Japan

[22] Filed: Apr. 11, 1973

[21] Appl. No.: 350,199

[30] Foreign Application Priority Data

Apr. 14, 1972 Japan.............................. 47-36850

[52] U.S. Cl............................. 260/243 C; 424/246
[51] Int. Cl.$^2$....................................... C07D 501/14
[58] Field of Search .............................. 260/243 C

[56] References Cited
UNITED STATES PATENTS

| | | | |
|---|---|---|---|
| 3,275,626 | 9/1966 | Morin et al. | 260/243 C |
| 3,507,861 | 4/1970 | Morin et al. | 260/243 C |
| 3,632,850 | 1/1972 | Garbrecht | 260/243 C |
| 3,668,201 | 6/1972 | Gutowski | 260/239.1 |
| 3,668,202 | 6/1972 | Foster et al. | 260/239.1 |

*Primary Examiner*—Nicholas S. Rizzo
*Assistant Examiner*—Jose Tovar
*Attorney, Agent, or Firm*—Flynn & Frishauf

[57] ABSTRACT

A novel ester of 7-acylamido-3-methyl-cepham-4-carboxylic acid derivative and a process for the preparation thereof which comprises reacting penicillin sulfoxide ester with the metal halide, and a novel 7-acylamido-3-methyl-cepham-4-carboxylic acid derivative and a process for the preparation thereof which comprises reacting penicillin sulfoxide ester with the metal halide and decomposing the resultant in a reductive atmosphere.

11 Claims, No Drawings

3-HALO-CEPHALOSPORINS

This invention relates to novel cephalosporin type antibiotics and methods for producing the same. More particularly, the present invention relates to novel 7-acylamido-3-halo-3-methyl-cepham-4-carboxylic acids and esters thereof. The present invention also relates to a method for producing 7-acylamido-3-halo-3-methyl-cepham-4-carboxylic acids and esters thereof.

The compounds of the present invention are represented by the following general formula:

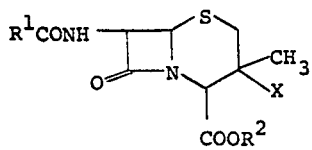

wherein R¹ represents benzyl or phenoxymethyl radical, R² represents hydrogen atom, alkyl, benzyl, p-nitrobenzyl or 2,2,2-trichloroethyl radical, and X represents a halogen atom.

The object compounds of this invention are not only novel cephalosporin antibiotics having antibiotic property per se but also novel useful compounds as intermediates for the preparation of several kinds of cephalosporin type antibiotics.

As described in Example 13, when these compounds are subjected to dehydrohalogenation by use of a base and then to hydrolysis, the corresponding 7-acylamido-3-methyl-Δ³-cephem-4-carboxylic acids which are known as useful cephalosporin antibiotics per se can be obtained. These compounds can be also used as intermediates to give more useful cephalosporin antibiotics, for example, cephalexin. More particularly, the cephalexin can be obtained from the above 7-acylamido-3-methyl-Δ³-cephem-4-carboxylic acid by a known method, for example, the method which is described in the specification of patent publication (Laid Open No. 42795/1972) of Bristol-Myers Company Ltd., of Japan which is as follows: The above 7-acylamido-3-methyl-Δ³-cephem-4-carboxylic acid is esterificated to trimethylsibyl ester and said ester is treated with phosphoric pentachloride so that the acylamido substituent thereof is changed into a corresponding imidochloride substituent. This imidochloride substituted compound is subjected to alcoholysis and hydrolysis to give 7-amino-3-methyl-Δ³-cephem-4-carboxylic acid, and this compound is changed into cephalexin by treating with a phenylglycinating agent, such as, phenylglycine chloride hydrochloride.

This invention relates especially to a process for the preparation of a 7-acylamido-3-halo-3-methyl-cepham-4-carboxylic acid esters having the general formula;

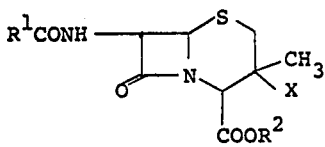

wherein R¹ represents a benzyl or phenoxymethyl radical, R² represents an alkyl, benzyl, p-nitrobenzyl or 2,2,2-trichloroethyl radical, and X represents a halogen atom, which comprises the reaction of a penicillin sulfoxide ester having the general formula:

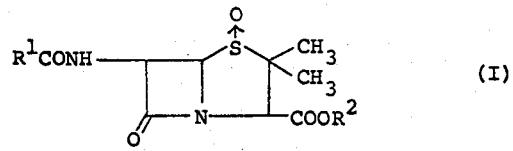

wherein R¹ and R² are the same as above, with a metal halide having the general formula:

MX$_n$ wherein M represents a metal atom, $n$ is an integer of 1 to 5, X is a halogen atom.

Furthermore, this invention relates especially to a 7-acylamido-3-halo-3-methyl-cepham-4-carboxylic acid derivative having the general formula:

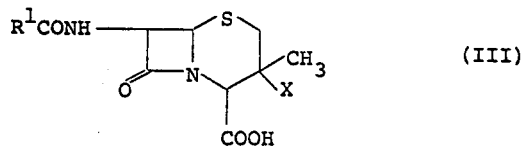

wherein R¹ and X are the same as above, which comprises the reaction of a penicillin sulfoxide ester having the general formula:

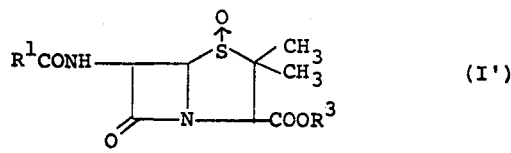

wherein R¹ is the same as above, and R³ represents benzyl, p-nitrobenzyl or 2,2,2-trichloroethyl radical, with a metal halide having the general formula:

MX$_n$ wherein M, X and $n$ are the same as above, and decomposing in a reductive atmosphere the resulting compound having the general formula:

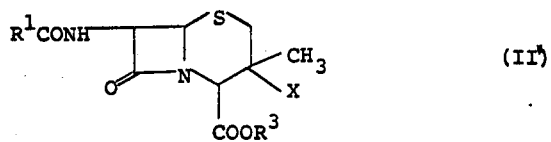

wherein R¹, R³ and X are the same as above.

In this invention, by reacting a 6-acylamido-penicillanic acid sulfoxide ester having the above formula (I) with a metal halide having the above formula MX$_n$ in an inert solvent, the thiazoline ring of a penicillin compound are changed into the six-membered ring and a halogen substituent is introduced to this to give a 7-acylamido-3-halo-3-methyl-cepham-4-carboxylic acid ester having the formula (II) which is a 7-acylamido-cepham-4-carboxylic acid ester derivative. This compound is a peculiar cephalosporin type compound having a halogen atom in its cepham nucleus, and inhibits strongly the growth of gram-positive organisms in the form of an acid. The starting material, the 6-acylamidopenicillanic acid sulfoxide ester may be easily prepared from penicillin V, penicillin G or 6-aminopenicillanic acid. The reaction of the starting material, 6-acylamido-penicillanic acid sulfoxide ester with the metal halide is carried out in an inert solvent by heating at 70° – 130°C.

In metal halides, a zinc halide, stannous halide and mercuric halide may be referred to as being useful. Stannous chloride, bromide and iodide, zinc chloride, and mercuric chloride are particularly preferable. In such cases halo-substituted cepham carboxylic acid ester having the halogen atom corresponding to a used metal halide may be obtained. The amount of the metal halide used is practically, 1.0–2.0 mol per one mol of the starting material, 7-acylamidopenicillanic acid sulfoxide ester. An inert solvent used in the reaction is a solvent which easily dissolves the metal halides, and a purified dioxane is preferable.

The reaction may be accomplished in dioxane by heating with refluxing for 4 – 6 hours or by heating at 85° – 95°C for 7 – 10 hours.

The separation of a resulting compound from the reaction mixture may be carried out by usual methods to be applied in chemical synthesis, for example, column chromatography. In applying elution column chromatography using 30 – 50 parts by weight of silica gel (100 – 200 mesh) per one part by weight of the reactant and elution solvent consisting of a mixed solvent of benzene-ethyl acetate having a volume ratio of 10:1 – 1:1, the resultant may be separated into respective elute portions.

The elute portions containing a 7-acylamido-3-halomethyl-cepham-4-carboxylic acid ester having the general formula (II) as principal resultant may be easily detected by a detecting test reaction for halogen-containing compounds, for example, Beilstein copper wire reaction test or thin-layer layer chromatography. The results of measurement of Infrared spectra, NMR spectra and elementary analysis of these compounds agreed with the values corresponding to structures of the compounds.

The following compounds are non-limitive examples of halogen-containing cepham-caboxylic acid esters obtained by this invention:

7-phenoxyacetoamido-3-chloro(or bromo or iodo)-3-methyl-cepham-4-carboxylic acid methylester 7-phenoxyacetoamido-3-chloro(or bromo or iodo)-3-methyl-cepham-4-carboxylic acid benzylester 7-phenoxyacetoamido-3-chloro(or bromo or iodo)-3-methyl-cepham-4-carboxylic acid p-nitrobenzylester 7-phenoxyacetoamido-3-chloro(or bromo or iodo)-3-methyl-cepham-4-carboxylic acid 2,2,2-trichloroethylester 7-phenylacetoamido-3-chloro(or bromo or iodo)-3-methyl-cepham-4-carboxylic acid methylester 7-phenylacetoamido-3-chloro-3-methyl-cepham-4-carboxylic acid p-nitrobenzylester The esters of 7-acylamido-3-halo-3-methyl-cepham-4-carboxylic acid thus obtained yield novel cephalosporin antibiotics having the above general formula (III) through deesterification thereof.

Further, esters of 7-acylamido-3-halo-3-methyl-cepham-4-carboxylic acid give easily desacetoxycephalosporanic acid derivatives by dehydrohalogenation thereof, which is as follows:

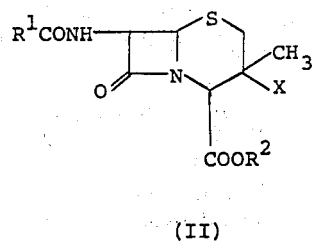 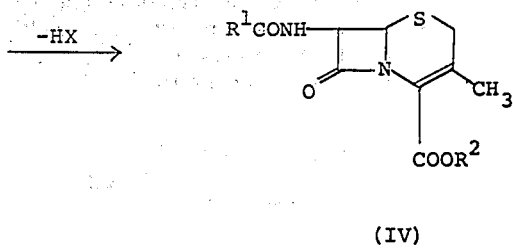

wherein $R^1$, $R^2$ and X are the same as above.

More detailedly, the halo-cepham compounds having the general formula (II) are dehydrohalogenated when heated in acetone with alkaline carbonate or reacted in benzene with trialkylamine or pyridine base, and give desacetoxycephalosporanic acid ester in good yield. The compounds having the formula (IV) are intermediates for the preparation of desacetoxycephalosporin type antibiotics which are represented by cephalexin. Therefore, esters of 7-acylamido-3-halo-3-methyl-cepham-4-carboxylic acid are also important intermediates for these antibiotics. comprises When suitable esters of 7-acylamido-3-methyl-cepham-4-carboxylic acid and suitable conditions for elimination reaction thereof are chosen, these esters may be decomposed and converted to the free acid thereof without receiving considerable effect to the cepham ring thereof. In case, 7-phenoxyacetoamido-3-chloro-3-methyl-cepham-4-carboxylic acid benzyl (or substituted benzyl) ester is subjected to catalytic reduction using palladium-active carbon catalysis or 2,2,2-trichloroethyl ester of the said carboxylic acid is subjected to decomposition using zinc dust with acetic acid, both of them give 7-phenoxyacetoamido-3-chloro-3-methyl-cepham-4-carboxylic acid. The said 7-phenoxyacetoamido-3-chloro-3-methyl-cepham-4-carboxylic acid inhibits the growth of Staphylococcus-aureus 209 P strain in a concentration of 12.5 γ/ml.

The following examples are to illustrate the present invention, but not to limit the invention thereto. For example, not only a phenoxyacetoamido and phenylacetoamido radical but also other acylamido radicals (e.g. α-carbobenzoxyaminophenylacetoamido radical) in 6-acylamino penicillanic acid sulfoxide ester of starting material play almost the same role in the invention.

EXAMPLE 1

In 150 ml of anhydrous dioxane 3.80 g (0.01 mol) of penicillin V suloxide methylester was allowed to react with 1.90 g (0.01 mol) of anhydrous stannous chloride with refluxing and stirring for 4 hours. The reaction mixture was then cooled and the insoluble material was filtered off. The filtrate was concentrated under reduced pressure and the residue was extracted with 100 ml of ethyl acetate. The extract was washed with water and dried. The residue (about 3.5 g) obtained after evaporation of ethyl acetate was purified by column chromatography using 150 g of silica gel (Wako Gel C-200: available from Wako Jynyaku Co., Ltd.). A mixed solvent of benzene-ethyl acetate (4:1) was used as elution solvent and the elute solution was collected in every 10 ml portion. Each portion was subjected to thin-layer chromatography and the portions containing the similar ingredient to each other are combined. The portions of Nos. 49 – 60 were concentrated. After a small amount of methanol is added thereto, the residue crystallized to give 0.24 g of 7-phenoxyacetoamido-$\Delta^3$-cephem-4-carboxylic acid ethylester as colourless needles having mp. 138.5° – 139.5°C (yield 7%). Also the elute portions of Nos. 63 – 88 were combined and concentrated under reduced pressure to give 1.18 g of colourless oily 7-phenoxyacetoamido-3-chloro-3-methyl-cepham-4-carboxylic acid methylester (yield 30%). This substance gave a positive Beilstein copper wire reaction test, and the following results of the measurement of Infrared spectra, NMR spectra and Mass spectra agreed with those expected from the structure.

IR (film); 1775 $cm^{-1}$ (lactam), 1737 $cm^{-1}$ (ester) and 1690, 1515 $cm^{-1}$ (amido).

NMR ($CDCl_3$): $\delta$ = 1.66 ppm (s3, 3-$CH_3$); 2.68, 3.65 (ABq2, J=15cps, 2-H); 3.74 (s3, ester-$CH_3$); 4.56 (s2, —$CH_2$—); 4.74 (s1, 4-H); 5.31 (d1, J=5cps, 6-H); 5.69 (dd1, J=5.9cps, 7-H); 7.03 (m5, phenyl); 7.58 (d1, J=9cps, amidoNH).

Mass Spectra; $M^+$ = 398 and 400

EXAMPLE 2

To 200 ml of anhydrous dioxane were added 4.56 g (0.01 mol) of penicillin V sulfoxide benzylester and 1.90 g (0.01 mol) of anhydrous stannous chloride, and the mixture was heated at 85° – 90°C with stirring and in a stream of nitrogen for 7 hours. The reaction mixture was distilled under reduced pressure and the resulting residue was stirred after 150 ml of ethyl acetate and 50 ml of 5% aqueous sodium hydrogen-carbonate were added thereto. The insoluble materials were filtered off and the ethyl acetate layer was separated from the filtrate. The ethyl acetate layer was washed with water and dried. The dried ethyl acetate was distilled off under reduced pressure. The residue (4.3 g) was purified by column chromatography using 140 g of silica gel (100 – 200 mesh). In this procedure, the elution was carried out by use of a mixed solvent of benzene-ethyl acetate (8:1) and elute solution was collected in every 10 ml portion. After investigating the portions by the method as described in Example 1, 1.10 g of 7-phenoxyacetoamido-3-chloro-3-methylcepham-4-carboxylic acid benzylester was obtained from the elute portions Nos. 32 – 44 (yield 23%). The measurement of NMR spectra agreed with those expected from the anticipated structure.

NMR ($CDCl_3$): $\delta$ = 1.57 ppm (s3, 3-$CH_3$); 2.68, 3.61 (ABq2, J=14.5cps, 2-H); 4.55 (s2, phenoxy-$CH_2$—); 4.78 (s1, 4-H); 5.20 (s2, ester-$CH_2$—); 5.31 (d1, J=4.5cps, 6-H); 5.69 (dd1 J=4.5, 9.5cps, 7-H); 7.02, 7.55 (m-phenyl); 7.62 (d1, J=9.5cps, amido NH).

EXAMPLE 3

In 200 ml of anhydrous dioxane were dissolved 5.01 g (0.01 mol) of penicillin V sulfoxide p-nitrobenzylester and 1.90 g (0.01 mol) of anhydrous stannous chloride with heating, and the mixture was heated with refluxing for 4 hours. After 2.0 g of active charcoal is added thereto, the reaction solution was cooled with stirring and filtered. After 10 g of silica gel (200 mesh) was added to the filtrate, the solvent was distilled away under reduced pressure. The absorbing silica gel thus obtained was put on the top of a column consisting of 150 g of silica gel and was subjected to elution with a mixed solvent of benzene-ethyl acetate (4:1). The elute was collected in every 25 g portion. Each portion was subjected to thin-layer chromatography to detect the eluted ingredient. The elute portions Nos. 15 – 18 were made together and distilled under reduced pressure to give 0.50 g of 7-phenoxyacetoamido-3-methyl-$\Delta^3$-cephem-4-carboxylic acid p-nitrobenzylesters crystals having mp. 189° – 191°C. The Infrared spectra and melting point of this substance agreed with those of the sample synthesized by other known methods. From the elute portions Nos. 20 – 30, 0.84 g of colourless solid was obtained, and which gave a positive Beilstein copper wire reaction.

Yield: 14%

Infrared spectra and NMR spectra of the obtained solid agreed with those of 7-phenoxyacetoamido-3-chloro-3-methylcepham-4-carboxylic acid p-nitrobenzylester:

IR ($CHCl_3$); 1775 (lactam), 1735 (ester) 1685, 1510 (amido), 1520, 1340 (nitro).

NMR ($CDCl_3$); 1.67 ppm (s3, 3-$CH_3$); 2.73, 3.63 (ABq2, J=14.5cps, 2-H); 4.56 (s2, phenoxy-$CH_2$—); 5.30 (m3, benzyl-$CH_2$-, H-6); 5.68 (dd1, J=4.5, 9.5cps, H-7);

EXAMPLE 4

To 150 ml of anhydrous dioxane were added 4.98 g (0.01 mol) of penicillin V sulfoxide 2,2,2-trichloroethylester and 1.90 g (0.01 mol) of anhydrous stannous chloride, and the mixture was heated with refluxing for 4 hours. The reaction solution was concentrated under reduced pressure and the residue was extracted with 200 ml of ethyl acetate. The extract was then washed with diluted hydrochloric acid. After 100 ml of 5% aqueous sodium hydrogencarbonate and 10 g of active charcoal were added to the ethyl acetate layer, the insoluble material was filtered off. The ethylacetate layer was separated from the filtrate, washed with water, dried and distilled under reduced pressure. The residue was subjected to column chromatography using 120 g of silica gel and a mixed solvent of benzene-ethyl acetate (6:1). In the same manner as described in Example 1, 1.37 g of 7-phenoxyacetoamido-3-chloro-3-methylcepham-4-carboxylic acid 2,2,2-trichloroethylester was obtained.

NMR ($CDCl_3$); $\delta$ = 1.92 ppm (s3, 3-$CH_3$); 2.88, 3.82 (ABq2, J=15cps, 2-H); 4.70 (s2, phenoxy-$CH_2$—); 4.96 (s2, ester-$CH_2$—); 5.04 (s1, 4-H); 5.45 (d1, J=4.5cps, 6-H); 5.83 (dd1, J=4.5, 9.5cps, 7-H); 7.00 (m5, phenyl); 7.67 (d1, J=9.5cps, amidoNH).

EXAMPLE 5

A mixture of 3.80 g (0.01 mol) of penicillin V sulfoxide methylester and 3.91 g (0.01 mol) of stannous iodide monohydrate was heated with refluxing and stirring in anhydrous dioxane for 4 hours. The reaction mixture was filtered to remove the insoluble materials therefrom, and the filtrate was concentrated under reduced pressure. The residue obtained was extracted with ethyl acetate. The extract was washed with a solution of sodium thiosulfate and water, and dried. The ethyl acetate was distilled off under reduced pressure and the residue was purified by column chromatography using 120 g of silica gel (100 – 200 mesh) and a mixed solvent of benzene-ethyl acetate (4:1). The elute was collected in portions and concentrated. After making together the portions which gave a positive Beilstein copper wire test and in which only a single ingredient was found by thin-layer chromatography, the resultant was treated in the same manner as described above. There was obtained 2.70 g of colourless oily 7-phenoxyacetoamido-3-iodo-3-methyl-cepham-4-carboxylic acid methylester.

Yield, 55%.

The measurement of NMR spectra and Infrared spectra were as follows:

NMR (CDCl$_3$); δ = 2.14 ppm (s3, 3-CH$_3$); 2.72, 3.02 (ABq2, J=15cps, 2-H); 3.75 (s3, ester, CH$_3$); 4.57 (s2, —CH$_2$—); 4.87 (s1, 4-H); 5.28 (d1, J=4.5cps, 6-H); 5.63 (dd1, J=4.5, 9.5cps, 7-H); 7.00 (m5, phenyl); 7.65 (d1, J=9.5, amido NH).

IR (film); 1773 (lactam), 1736 (ester) 1690, 1520 cm$^{-1}$ (amido).

EXAMPLE 6

A mixture of 1.03 g (0.002 mol) of penicillin V sulfoxide p-nitrobenzylester and 0.76 g (0.002 mol) of stannous iodide monohydrate was heated with refluxing and stirring in 40 ml of anhydrous dioxane for 4 hours. The reaction mixture was cooled and filtered to remove the insoluble materials therefrom. The filtrate was distilled under reduced pressure. The residue was adsorbed in 3.0 g of silica gel (100 – 200 mesh) and the silica gel was put on the top of column consisting of 30 g of the same silica gel. The elution was carried out by a mixed solvent of benzene-ethyl acetate (4:1) and collected in portions. The portions in which only a single ingredient was found by thin-layer chromatography and which gave a positive Beilstein copper wire reaction test were made together. From the resulting portion, there was obtained 0.49 g of 7-phenoxyacetoamido-3-iodo-3-methyl-cepham-4-carboxylic acid p-nitrobenzylester in light-brown powder.

Yield, 39%.

Elementary analysis: Found: C; 45.97%, H; 3.81%, N; 6.83% Calculated for $C_{23}H_{23}N_3O_7SI$: C; 45.18%, H; 3.63%, N; 6.87%.

The measurement of NMR spectra were as follows:

NMR (CDCl$_3$); δ = 2.13 ppm (s3, 3-CH$_3$); 2.72, 3.06 (ABq2, J=15cps, 2-H); 4.61 (s2, phenoxy-CH$_2$—); 4.94 (s1, 4-H); 5.33 (m3, 6-H, benzyl-CH$_2$—); 5.70 (dd1, J=4.5, 9.5 7-H).

EXAMPLE 7

A mixture of 0.76 g (0.002 mol) of penicillin V sulfoxide methylester and 0.54 g (0.002 mol) of mercuric chloride was heated with refluxing in 25 ml of anhydrous dioxane for 11 hours. Dioxane was distilled from the reaction mixture under reduced pressure. The residue was extracted with 30 ml of ethyl acetate. The extract was washed with water and dried. The ethyl acetate was distilled off from the extract under reduced pressure. The residue was eluted and purified by column chromatography using 20 g of silica gel (100 – 200 mesh) and a mixed solvent of benzene-ethyl acetate (4:1). The elute was collected in portions. The elute portions giving a positive Beilstein copper wire reaction test were made together. The resultant was treated as above described to give 0.20 g of 7-phenoxyacetoamido-3-chloro-3-methyl-cepham-4-carboxylic acid methylester (yield 25%). The measurement of Infrared spectra and NMR spectra of this substance agreed with those of the sample obtained in Example 1.

EXAMPLE 8

In 30 ml of anhydrous dioxane, 0.76 g (0.002 mol) of penicillin V sulfoxide methylester and 0.56 g of stannous bromide was heated at 90° – 95°C for 8 hours. The reaction mixture was filtered and the filtrate was distilled under reduced pressure. The residue was adsorbed in 2.0 g of silica gel (100 – 200 mesh) and the silica gel was put on the top of the column consisting 30 g of the same silica gel. The column was eluted with a mixed solvent of benzene-ethyl acetate (4:1). The elute was collected in portions and the portions giving a positive Beilstein copper wire reaction test were made together. It gave 0.17 g of colourless oily 7-phenoxyacetoamido-3-bromo-3-methyl-cepham-4-carboxylic acid methylester.

Yield, 19%.

EXAMPLE 9

In anhydrous dioxane was dissolved 0.73 g (0.002 mol) of penicillin G sulfoxide methylester. After 0.27 g (0.002 mol) of zinc chloride was added thereto, the solution was heated at 85° – 90°C for 8 hours. The reaction mixture was distilled under reduced pressure and the residue was extracted with 50 ml of ethyl acetate. The extract was washed with water and dried and distilled under reduced pressure. The oily residue was purified by column chromatography consisting 25 g of silica gel (100 – 200 mesh). The elution was carried out by the use of a mixed solvent of benzene-ethyl acetate (3:1) and the elute was collected in every 10 ml portion. Each portion was concentrated. The portions giving a positive Beilstein copper wire reaction were made together to give 0.10 g of 7-phenylacetoamido-3-chloro-3-methyl-cepham-4-carboxylic acid methylester (yield, 13%). The following NMR spectra and Infrared spectra agreed with those expected from the anticipated structure:

NMR (CDCl$_3$); δ = 1.66 ppm (s3, 3-CH$_3$); 2.72, 3.61 (ABq2, J=14.5cps, 2-H); 3.65 (s2, benzyl-CH$_2$—); 3.79 (s3, ester-CH$_3$); 4.72 (s1, 4-H); 5.27 (d1, J=4.5cps, 6-H); 5.63 (dd1, J=4.5, 9cps, 7-H); 6.79 (d1, J=9cps, amidoNH); 7.45 (s5, phenyl).

IR (film); 1775 (lactam) 1740 (ester) 1660, 1527 (amido).

EXAMPLE 10

To 30 ml of dioxane were added 0.73 g (0.002 mol) of penicillin G sulfoxide methylester and 0.78 g of stannus iodide monohydrate. The mixture was heated with refluxing for 5 hours. The reaction mixture was cooled and filtered. The filtrate was distilled under reduced pressure. The residue was purified by the column chromatography using the same method as in Example 9. The elute portions giving a positive Beilstein copper wire reaction test were made together to give 0.09 g of light-brown oily 7-phenyl-acetoamido-3-iodo-3-methyl-cepham-4-carboxylic acid methylester. The following NMR spectra agreed with those expected from the anticipated structure:

NMR (CDCl$_3$); δ = 2.14 ppm (s3, 3-CH$_3$); 2.66, 3.04 (ABq2, J=15cps, 2-H); 3.78 (s3, ester-CH$_3$); 3.69 (s2, benzyl-CH$_2$—); 4.82 (s1, 4-H); 5.27 (d1, J=4.5cps, 6-H); 5.59 (dd1, J=4.5, 9.5cps, 7-H); 6.84 (d1, J=9.5cps, amidoNH); 7.41 (s5, phenyl).

EXAMPLE 11

In 30 ml of ethyl acetate was dissolved 470 mg of 7-phenoxyacetoamido-3-chloro-3-methyl-cepham-4-carboxylic acid p-nitrobenzylester. To the solution was added 470 mg of 5% palladium-charcoal and the solution was stirred for 19 hours in a stream of hydrogen. After the catalyst was filtered off from the reaction mixture, the filtrate was extracted with 50 ml of 2% aqueous sodium hydrogencarbonate solution. After the aqueous layer was separated and adjusted to pH 2 by adding diluted hydrochloric acid, the aqueous layer was extracted again with ethyl acetate. The ethyl acetate layer was washed with water, dried and distilled under reduced pressure. There was obtained 179 mg of 7-phenoxyacetoamido-3-chloro-3-methyl-cepham-4-carboxylic acid as a colourless powder (yield, 15%). The following NMR spectra agreed with those expected from the anticipated structure:

NMR (CDCl$_3$); δ = 1.80 ppm (s3, 3—CH$_3$); 2.73, 3.70 (ABq2, J=15cps, 2-H); 4.60 (s2, phenoxy-CH$_2$—); 4.75 (s1, 4-H); 5.34 (d1, J=4.5cps, 6-H); 5.66 (dd1, J=4.5, 9cps, 6-H); 7.01 (m5, phenyl); 7.62 (d1, J=9cps, amidoNH); 9.74 (s1, COOH).

EXAMPLE 12

In 10 ml of glacial acetic acid was dissolved 510 mg of 7-phenoxyacetoamido-3-chloro-3-methyl-cepham-4-carboxylic acid 2,2,2-trichloro-ethylester. To the solution was added 0.65 g of zinc dust with ice-cooling. The resultant was further stirred for 3 hours at the same temperature. The insoluble material was filtered off from the reaction mixture and the filtrate was extracted with ethyl acetate. The extract is washed with 5% hydrochloric acid and water, dried, and distilled under reduced pressure. The residue thus obtained was extracted with 2% aqueous sodium hydrogencarbonate solution and ethyl acetate. The aqueous layer was separated and adjusted to pH 2 by adding drops of diluted hydrochloric acid, and then extracted again with ethyl acetate. The ethyl acetate layer was dried and distilled under reduced pressure. There was obtained 123 mg of colourless powders, and of which NMR spectra agreed with those of the sample obtained in Example 1.

EXAMPLE 13

In 30 ml of anhydrous benzene was dissolved 530 mg of 7-phenoxyacetoamido-3-chloro-3-methyl-cepham-4-carboxylic acid methylester. To the solution was added 200 mg of triethylamine. The resulting solution was heated with refluxing on a water bath for 4 hours. The reaction mixture was cooled and insoluble triethylamine hydrochloride was filtered off. The filtrate was distilled under reduced pressure. The residue was recrystallized from a mixed solution of methanol-water to give 391 mg of 7-phenoxyacetoamido-3-methyl-Δ$^3$-cephem-4-carboxylic acid methylester in colourless needles (yield, 81%). The melting point, infrared spectra and NMR spectra of this substance agreed with those of the substance obtained by the other known method and in Example 1.

NMR (CDCl$_3$); δ = 2.12 ppm (s3, 3—CH$_3$); 3.16, 3.48 (ABq2 J=18cps, 2-H); 3.80 (s3, ester-CH$_3$); 4.52 (s2, phenoxy-CH$_2$—); 4.97 (d1, J=4.5cps, 6-H); 5.80 (dd1 J=4.5, 9cps, 7-H); 6.84 – 7.45 (m6, phenyl and amidoNH).

What is claimed is:

1. A compound of the formula:

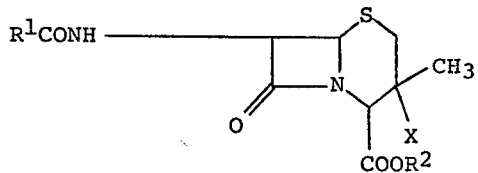

wherein R$^1$ represents benzyl or phenoxymethyl, R$^2$ represents hydrogen, methyl, benzyl, p-nitrobenzyl or 2,2,2-trichloroethyl, and X is chlorine, bromine or iodine.

2. 7-phenoxyacetoamido-3-chloro-3-methyl-cepham-4-carboxylic acid methylester.

3. 7-phenoxyacetoamido-3-chloro-3-methyl-cepham-4-carboxylic acid benzylester.

4. 7-phenoxyacetoamido-3-chloro-3-cepham-4-carboxylic acid p-nitrobenzylester.

5. 7-phenoxyacetoamido-3-chloro-3-methyl-cepham-4-carboxylic acid 2,2,2-trichloroethylester.

6. 7-phenoxyacetoamido-3-iodo-3-methyl-cepham-4-carboxylic acid methylester.

7. 7-phenoxyacetoamido-3-iodo-3-methyl-cepham-4-carboxylic acid p-nitrobenzylester.

8. 7-phenoxyacetoamido-3-bromo-3-methyl-cepham-4-carboxylic acid methylester.

9. 7-phenylacetoamido-3-chloro-3-methyl-cepham-4-carboxylic acid methylester.

10. 7-phenylacetoamido-3-iodo-3-methyl-cepham-4-carboxylic acid methylester.

11. 7-phenoxyacetoamido-3-chloro-3-methyl-cepham-4-carboxylic acid.

* * * * *

Notice of Adverse Decision in Interference

In Interference No. 101,857, involving Patent No. 3,963,712, M. Koyama and S. Seki, 3-HALO-CEPHALOSPORINS, final judgment adverse to the patentees was rendered Jan. 30, 1989, as to claims 1-11.

*[Official Gazette May 30, 1989]*